United States Patent
Kumar et al.

(10) Patent No.: US 6,921,839 B2
(45) Date of Patent: Jul. 26, 2005

(54) SYNTHESIS OF N,N-DIMETHYL-3-(4-METHYL) BENZOYL PROPIONAMIDE A KEY INTERMEDIATE OF ZOLPIDEM

(75) Inventors: Yatendra Kumar, Gurgaon (IN); Mohan Prasad, Gurgaon (IN); Azok Nath, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 10/363,377
(22) PCT Filed: Aug. 28, 2001
(86) PCT No.: PCT/IB01/01558
§ 371 (c)(1), (2), (4) Date: Sep. 17, 2003
(87) PCT Pub. No.: WO02/18303
PCT Pub. Date: Mar. 7, 2002

(65) Prior Publication Data
US 2004/0054230 A1 Mar. 18, 2004

(30) Foreign Application Priority Data
Aug. 29, 2000 (IN) .................................. 782/DEL/2000

(51) Int. Cl.[7] ............................................. C07C 231/02
(52) U.S. Cl. ...................................................... 564/139
(58) Field of Search ......................................... 564/139

(56) References Cited

U.S. PATENT DOCUMENTS

| 4,382,938 A | 5/1983 | Kaplan et al. | 424/256 |
| 2002/0183522 A1 | 12/2002 | Sauter et al. | 546/112 |
| 2004/0054230 A1 | 3/2004 | Kumar et al. | 546/133 |

FOREIGN PATENT DOCUMENTS

| CA | 2 445 766 A1 * | 11/2002 | C07D/471/04 |
| DE | 101 21 638 | 11/2002 | C07D/471/02 |
| EP | 1 005 863 | 6/2000 | A61K/31/415 |
| EP | 1 064 936 | 1/2001 | A61K/9/20 |
| WO | WO 01/80857 | 11/2001 | A61K/31/44 |

OTHER PUBLICATIONS

Trapani, G et al. "Synthesis and Binding Affinity of 2–Phenylimidazol 1,2–alpyridine derivatives for both Central and Peripheral Benzodiazepine Receptors. A New Series of High–Affinity and Selective Ligands for the Peripheral Type," *J. Med. Chem.*, 40, pp. 3109–3118 (1997).

Huffman, J.W., "A New Synthetic Route to Methoxytetralones," *J. Org. Chem.*, 24, pp. 1759–1763 (1959).

* cited by examiner

*Primary Examiner*—Brian Davis
(74) *Attorney, Agent, or Firm*—Jayadeep R. Deshmukh, Esq.

(57) ABSTRACT

The present invention relates to an improved and industrially advantageous process for the preparation of N,N-dimethyl-3-(4-methyl)benzoyl propionamide of Formula I,

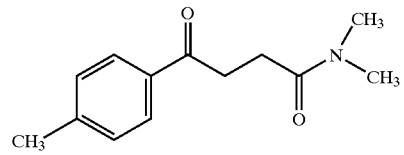

FORMULA I which is a key intermediate in the synthesis of zolpidem hemitartrate, a non-benzodiazepine hypnotic agent. The process includes reacting 3-(4-methyl)-benzoyl propionic acid of Formula IV, with alkyl chloroformate or pivaloyl chloride to get a mixed anhydride of Formula V; and reacting the mixed anhydride of Formula V with dimethylamine of Formula VI to get the N,N-dimethyl-3-(4-methyl) benzoyl propionamide of Formula I.

17 Claims, No Drawings

SYNTHESIS OF N,N-DIMETHYL-3-(4-METHYL) BENZOYL PROPIONAMIDE A KEY INTERMEDIATE OF ZOLPIDEM

This application is a 371 of PCT/IB01/01558 filed Aug. 28, 2001.

FIELD OF THE INVENTION

The present invention relates to an improved and industrially advantageous process for the preparation of N,N-dimethyl-3-(4-methyl)benzoyl propionamide of Formula I,

FORMULA I

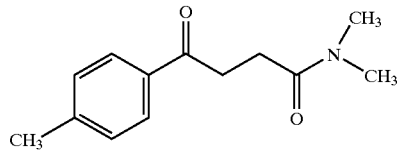

which is a key intermediate in the synthesis of zolpidem hemitartrate, a non-benzodiazepine hypnotic agent.

BACKGROUND OF THE INVENTION

Chemically, zolpidem hemitartrate is N,N,6-trimethyl-2-(4-methyl-phenyl)imidazo[1,2-a]pyridine-3-acetamide L-(+)-hemitartrate of Formula II.

FORMULA II

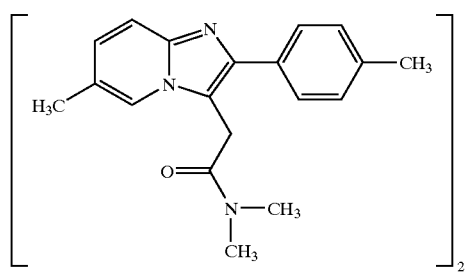

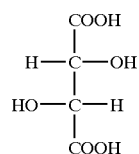

Zolpidem is known from European Patent No. 50,563 (U.S. Pat. No. 4,382,938 is its equivalent in the United States) assigned to Synthelabo. The pharmacological profile of this compound is characterized by a strong hypnotic effect, together with weak anticonvulsant and muscle-relaxant properties, showing selectivity for benzodiazepine receptors with the biochemical characteristics and regional distribution of the benzodiazepine one subtype. While zolpidem is a hypnotic agent with a chemical structure unrelated to benzodiazepines, barbiturates, or other drugs with known hypnotic properties, it interacts with gamma-aminobutyric acid (GABA)-benzodiazepine receptor complex and shares some of the pharmacological properties of the benzodiazepines. The selective binding of zolpidem on the omega-1 receptor may explain the relative absence of myorelaxant and anticonvulsant effects in animal studies. Zolpidem shows both high affinity and selectivity toward non-benzodiazepine-2 receptors which means improved activity and/or fewer side effects for the treatment of anxiety, sleep disorders and convulsions.

A previously known general method for the synthesis of the intermediate N,N-dialkyl-3-benzoyl-propionamide of Formula III,

FORMULA III

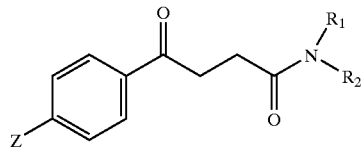

wherein for the zolpidem intermediate Z=$CH_3$ and $R_1$=$R_2$=$CH_3$ was reported in *J. Med. Chem.*, 40, 3109–3118 (1997) which involves reaction of 3-benzoyl propionic acid of Formula IV,

FORMULA IV

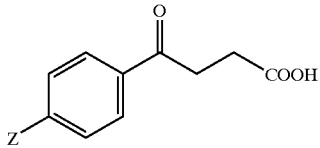

[Z=$CH_3$, prepared by the method as described in *J. Org. Chem.*, 24, 1759–1763 (1959)] with the required dialkylamines (dimethylamine for Zolpidem) in the presence of ethyl 1,2-dihydro-2-ethoxy-1-quinoline carboxylate (EEDQ) in tetrahydrofuran at reflux. Evaporation of the solvent under reduced pressure and pH adjustment gives the crude product which in turn is purified by column chromatography.

The above method described in the prior art for the manufacture of the desired compound of Formula I suffers from the following limitations:

The reaction conditions are unsafe which are burdened with the risk of explosion and fire as the reaction makes use of the solvent tetrahydrofuran at reflux temperature.

The process requires commercially limited available and costly raw material such as ethyl 1,2-dihydro-2-ethoxy-1-quinoline carboxylate (EEDQ).

The process involves column chromatography for purification of the desired intermediate which is not practically feasible at the commercial scale.

It is an object of the present invention to solve the problems associated with the prior art, and to provide an improved and efficient method for the preparation of pure N,N-dimethyl-3-(4-methyl) benzoyl proplonamide of Formula I. The process provides obvious benefits with respect to economics, convenience to operate at a commercial scale and does not require chromatography to purify the desired product.

More particularly, the present invention relates to a process for the preparation of N,N-dimethyl-3-(4-methyl) benzoyl propionamide of Formula I, comprising reacting the 3-(4-methyl)-benzoyl propionic acid of Formula IV (wherein Z is methyl) with alkyl chloroformate or pivaloyl chloride to give a mixed anhydride of Formula V,

FORMULA V

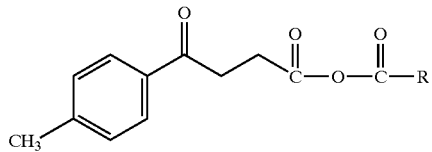

wherein R is alkyl or substituted alkyl, preferably methyl, ethyl or tertiary butyl, in a suitable solvent in the presence of an organic base, the mixed anhydride of Formula V on further reaction with dimethylamine of Formula VI,

FORMULA VI

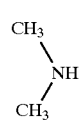

affords the desired product of Formula I.

The alkyl chloroformate is selected from the group consisting of methyl chloroformate, ethyl chloroformate and butyl chloroformate; the methyl chloroformate being preferred. The alkyl chloroformate or pivaloyl chloride is suitably used in an amount of 1.0–2.0 molar equivalents of compound of Formula IV, and preferably in an amount of 1.1 to 1.5 molar equivalents.

The term "suitable solvent" includes chlorinated solvents, aromatic solvents, esters and mixture(s) thereof. Preferably, the solvent may be selected from the group consisting of dichloromethane, dichloroethane, chloroform, toluene, ethyl acetate and mixture(s) thereof. The solvent is suitably used in an amount of 5 to 20 times of weight of the compound of Formula IV, and preferably in an amount 10 to 15 times.

The suitable organic base is selected from the group comprising trimethylamine, triethylamine, picolines, pyridine, pyridine derivatives, morpholine and morpholine derivatives. The organic base is suitably used in an amount of 1.0 to 2.0 molar equivalents of the compound of Formula IV and preferably in an amount 1.1 to 1.5 molar equivalents.

The reaction of "mixed anhydride" of Formula V (wherein R is the same as defined earlier) with dimethylamine is carried out at a selected temperature range of −25 to 40° C., preferably 0 to 30° C. during a period of 15 minutes to several hours, preferably for about 15 minutes to 1 hour. The desired compound, N,N-dimethyl-3-(4-methyl) benzoyl propionamide of Formula I is isolated by removal of the solvent completely from the organic layer after washing with water/aqueous sodium carbonate solution and stirring the residue with n-hexane. The solid separated is filtered, washed with n-hexane and dried to get the pure desired compound.

In the following section preferred embodiments are described by way of examples to illustrate the process of this invention. However, these are not intended in any way to limit the scope of the present invention.

Preparation of N,N-Dimethyl-3-(4-Methyl)Benzoyl Propionamide

EXAMPLE 1

3-(4-Methyl)-benzoyl propionic acid (50 gm) was suspended in ethyl acetate (500 ml) and it was cooled to 0–5° C. To it was added triethylamine (28.93 gm) at 0–5° C. to get a clear solution. Pivaloyl chloride (34.52 gm) was added to the clear solution during a period of 15 minutes keeping temperature at 0–5° C. The resulting reaction mixture was stirred at 0–5° C. for about 30 minutes. To this was added dimethyl amine (60 gm, 40% solution in water) in one lot taken in 250 ml of ethyl acetate at −10 to 0° C. After stirring R at 0 to 10° C. for about 30 minutes, the reaction mixture was washed with water, aqueous sodium carbonate solution (10% w/v) and water. The organic layer was dried over anhydrous sodium sulphate and solvent was removed under reduced pressure. The residue so obtained was stirred with hexane and the solid separated was filtered and dried to get 48.5 gm (yield 85% of the theory) of pure title compound (purity by HPLC 99.8%).

EXAMPLE 2

Triethylamine (28.93 gm) was added to a solution of 3-(4-methyl)-benzoyl propionic acid (50 gm) dissolved in methylene chloride (500 ml) at about −5° C. The resulting reaction mixture was further cooled to about −10° C. and pivaloyl chloride (34.52 gm) was added to it during a period of about 15 minutes keeping the temperature at −10 to 0° C. The resulting reaction mixture was stirred at −2 to 0° C. for about 30 minutes and dimethyl amine (60 gm, 40% w/v solution in water) was added to it in one lot. The reaction mixture thus obtained was further stirred at 25–30° C. for about 30 minutes, washed with water, aqueous sodium carbonate solution (10% w/v) and finally with water. The organic layer was dried over anhydrous sodium sulphate and concentrated under vacuum. Hexane (200 ml) was added to the residue; the solid separated was filtered and dried to get 46.8 gm (82%) of the pure product (Purity by HPLC 99.7%).

EXAMPLE 3

Triethylamine (14.5 gm) was added to solution of 3-(4-methyl)-benzoyl propionic acid (25 gm) in chloroform (250 ml) at 0–5° C. The solution thus obtained was cooled to −5° C. and pivaloyl chloride (17.3 gm) was added to it over a period of about 20 minutes keeping the temperature at −5 to 0° C. The reaction mixture thus obtained was stirred at −5 to 0° C. for about 30 minutes and to it was added dimethylamine (30 gm, 40% w/v solution in water) at −5 to 0° C. during a period of about 15 minutes. The reaction mixture thus obtained was further stirred at −5 to 0° C. for about 15 minutes, washed with water, 10% w/v aqueous sodium carbonate solution and finally with water. The organic layer was concentrated, and the residue was stirred with hexane. The solid separated was filtered and dried to get 23.5 gm (yield 82.5% of the theory) of the pure desired product (purity by HPLC=99.8%).

EXAMPLE 4

To a solution of 3-(4-methyl)-benzoylpropinoic acid (25 gm) in methylene chloride (250 ml) at 0° C. was added triethylamine (14.5 gm). The resulting reaction mixture was cooled to −25° C. and ethylchloroformate (14.2 gm) was added to it at −25 to −20° C. during a period of about 10 minutes. The reaction mixture thus obtained was stirred at −25 to −20° C. for about 30 minutes and dimthylamine (30 gm, 40% w/v solution in water) was added at about −25° C. during a period of about 10 minutes. The reaction mixture thus obtained was stirred at the −10 to 0° C. for about 30 minutes and raised the temperature to about 25–30° C. The resulting reaction mixture was washed with water, aqueous sodium carbonate solution (10% w/v) and finally with water. The organic layer was concentrated under vacuum and stirred with hexane (100 ml). The solid thus separated was filtered and dried to yield 23 gm (yield 80.7% of theory) of the desired product (purity by HPLC 99.8%).

While the present invention has been described in terms of its specific embodiments, certain modifications and equivalents will be apparent to those skilled in the art and are intended to be included within the scope of the present invention.

What is claimed is:

1. A process for the preparation of N,N-dimethyl-3-(4-methyl) benzoyl propionamide of Formula I,

FORMULA I

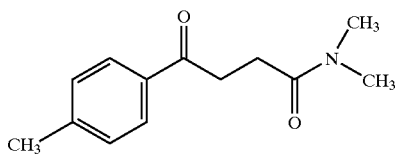

comprising reacting 3-(4-methyl)-benzoyl propionic acid of Formula IV,

FORMULA IV

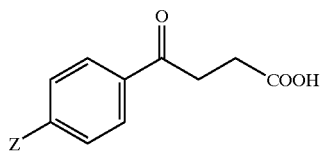

wherein Z is methyl, with alkyl chloroformate or pivaloyl chloride in a suitable solvent in the presence of an organic base to afford a mixed anhydride of Formula V,

FORMULA V

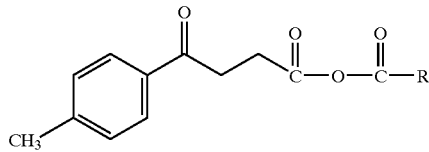

wherein R is alkyl or substituted alkyl; and further reacting the mixed anhydride of Formula V with dimethylamine of Formula VI,

FORMULA VI

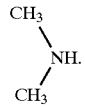

2. The process of claim 1, wherein the alkyl chloroformate is selected from the group consisting of methyl chloroformate, ethyl chloroformate and butyl chloroformate.

3. The process of claim 2, wherein the alkyl chloroformate is methyl chloroformate.

4. The process of claim 1, wherein the suitable solvent is selected from the group consisting of chlorinated solvents, aromatic solvents, esters and mixture(s) thereof.

5. The process of claim 4, wherein the solvent is selected from the group consisting of dichloromethane, dichloroethane, chloroform, toluene, ethyl acetate and mixture(s) thereof.

6. The process of claim 1, wherein the organic base is selected from the group consisting of trimethylamine, triethylamine, picolines, pyridine pyridine, derivatives, morpholine, morpholine derivatives and mixtures thereof.

7. The process of claim 1, wherein the alkylchloroformate is used in an amount of 1.0 to 2.0 molar equivalents of the compound of Formula IV.

8. The process of claim 1, wherein the solvent is used in amount of 5 to 20 times (by volume) of weight of the compound of Formula IV.

9. The process of claim 8, wherein the solvent is used in an amount of 10 to 15 times (by volume) of weight of the compound of Formula IV.

10. The process of claim 1, wherein the organic base is used in an amount of 1.0 to 2.0 molar equivalents of compound of Formula IV.

11. The process of claim 10, wherein the organic base is used in an amount of 1.1 to 1.5 molar equivalents of compound of Formula IV.

12. The process according to claim 1, wherein the reaction of mixed anhydride of Formula V with dimethylamine is carried out at a selected temperature range of −25 to 40° C.

13. The process according to claim 12, wherein the reaction of mixed anhydride of Formula V with dimethylamine is carried out at a temperature of about 0 to 30° C.

14. The process according to claim 1, wherein the reaction of mixed anhydride of Formula V with dimethyl amine is carried out for 15 minutes to several hours.

15. The process according to claim 14, wherein the reaction of mixed anhydride of Formula V with dimethylamine is carried out for 15 minutes to 1 hour.

16. The process of claim 1 further comprising suitable work up after the reaction is complete.

17. The process according to claim 16, wherein the work up comprises removal of the solvent from the organic layer and isolation of said product by stirring the remaining residue with hexane.

* * * * *

UNITED STATES PATENT AND TRADEMARK OFFICE
CERTIFICATE OF CORRECTION

PATENT NO. : 6,921,839 B2
DATED : July 26, 2005
INVENTOR(S) : Kumar et al.

It is certified that error appears in the above-identified patent and that said Letters Patent is hereby corrected as shown below:

Title page, Item [54] and Column 1, line 2,
Title, "PROPIONAMIDE A KEY" should read -- PROPIONAMIDE, A KEY --.

Title page,
Item [75], Inventors, "Azok" should read -- Asok --.
Item [56], References Cited, OTHER PUBLICATIONS,
"Trapani" reference, "Phenylimidazol 1,2" should read -- Phenylimidazol [1,2 --.

Column 1,
Line 26, "-phenyl)midazo" should read -- -phenyl)-imidazo --.

Column 2,
Line 57, "proplonamide" should read -- propionamide --.
Line 65, "comprising reacting the" should read -- comprising reacting --.

Column 4,
Line 59, "dimthylamine" should read -- dimethylamine --.

Column 6,
Line 14, "pyridine pyridine, derivatives" should read -- pyridine, pyridine derivatives --.
Line 21, "amount" should read -- an amount --.
Line 41, "dimethyl amine" should read -- dimethylamine --.

Signed and Sealed this

Fourth Day of October, 2005

JON W. DUDAS
*Director of the United States Patent and Trademark Office*